United States Patent [19]
Milani et al.

[11] 3,961,623
[45] June 8, 1976

[54] METHOD OF USING A DISPOSABLE ELECTRODE PAD

[75] Inventors: Dean L. Milani, Highland Park; Richard G. Kerwin, Prospect Heights, both of Ill.

[73] Assignee: Medical Research Laboratories, Inc., Niles, Ill.

[22] Filed: Jan. 17, 1975

[21] Appl. No.: 542,033

[52] U.S. Cl. .......................... 128/2.06 E; 128/417; 128/419 D; 128/DIG. 4
[51] Int. Cl.² ...................... A61B 5/05; A61H 31/00
[58] Field of Search ........ 128/417, 419 D, 404–406, 128/418, 2.06 E, 2.1 E, 172.1, DIG. 4, 416

[56] References Cited
UNITED STATES PATENTS

| | | | |
|---|---|---|---|
| 2,943,627 | 7/1960 | Howell | 128/DIG. 4 |
| 3,151,619 | 10/1964 | Sullivan | 128/418 |
| 3,601,126 | 8/1971 | Estes | 128/417 |
| 3,610,229 | 10/1971 | Zenkich | 128/417 |
| 3,702,613 | 11/1972 | Panico | 128/419 D |
| 3,774,592 | 11/1973 | Lahr | 128/2.1 E |
| 3,826,245 | 7/1974 | Funfstuck | 128/419 D |
| 3,828,766 | 8/1974 | Krasnow | 128/417 |

*Primary Examiner*—Robert W. Michell
*Assistant Examiner*—Lee S. Cohen
*Attorney, Agent, or Firm*—Robert M. Wolters

[57] ABSTRACT

A disposable electrode pad is provided for a defibrillator electrode. The pad is saturated with electrically conductive greasy material, sometimes known as electrogel. The pad is designed for adhesive or other securing to the electrode, and the pad is covered with a tear-off aluminum sheet cover to protect the integrity and sanitation of the pad, while still allowing sufficient electrical conductivity for monitoring a patient's heartbeat through the electrode.

1 Claim, 11 Drawing Figures

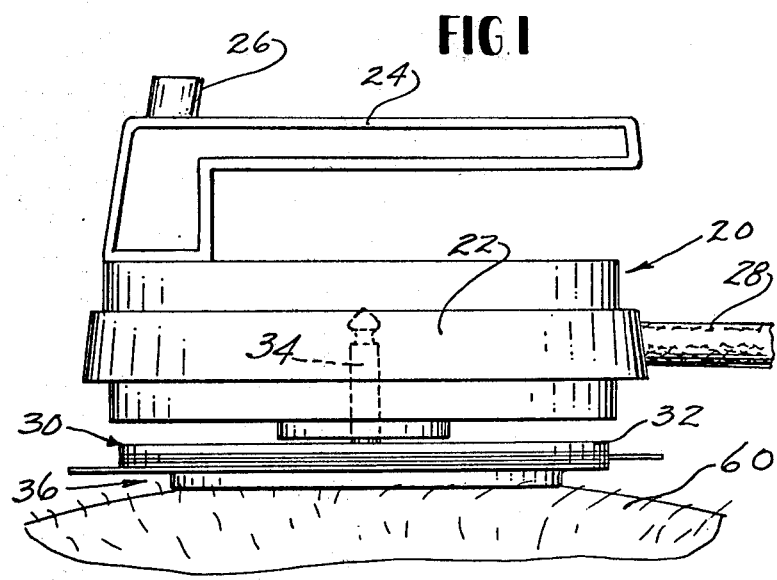
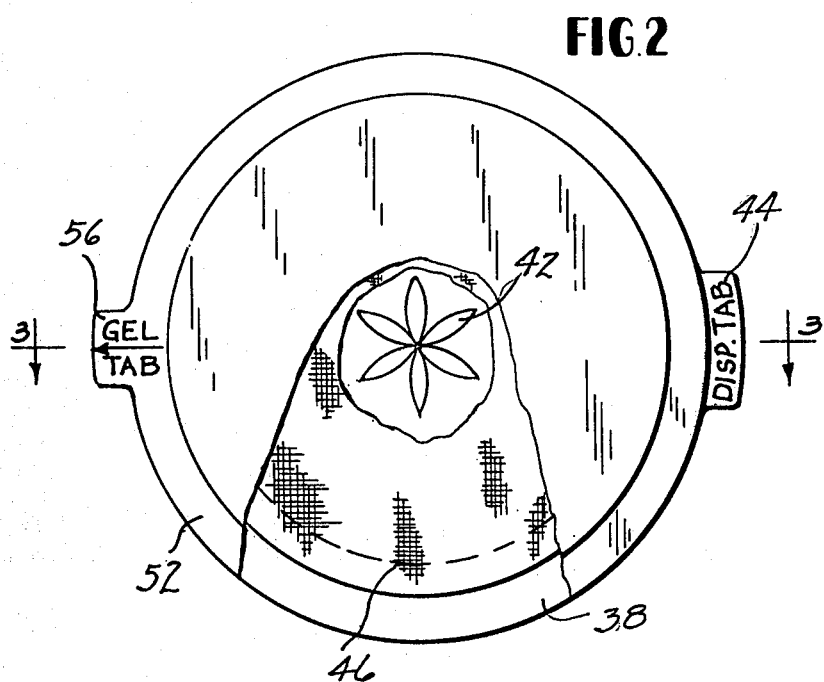
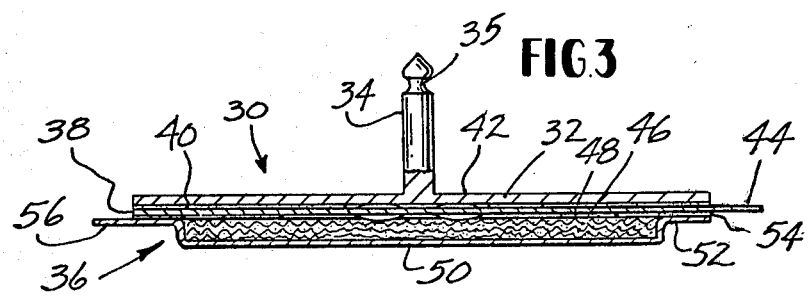

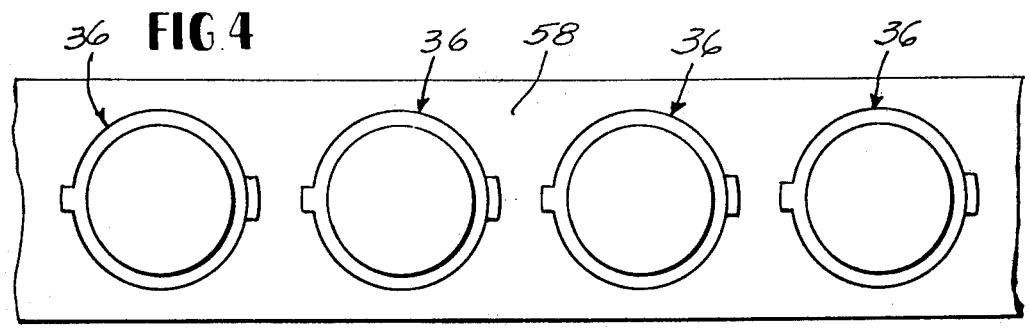
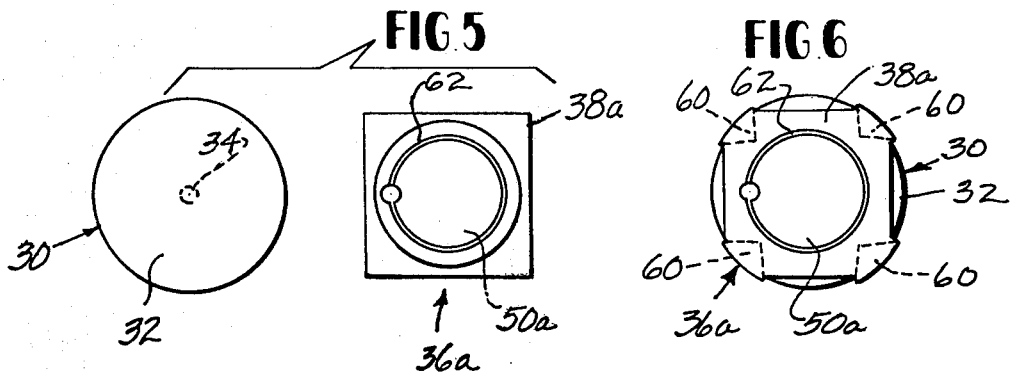
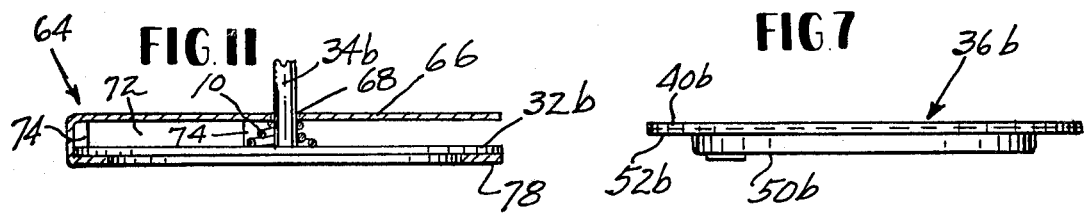
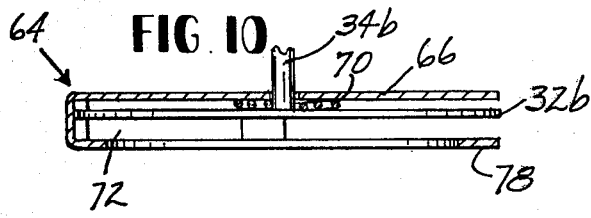
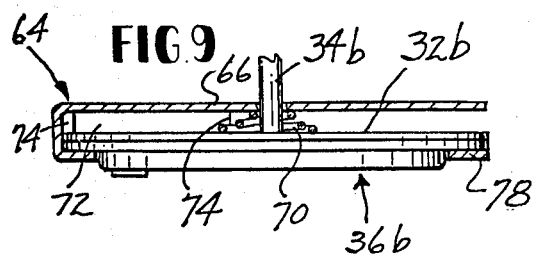
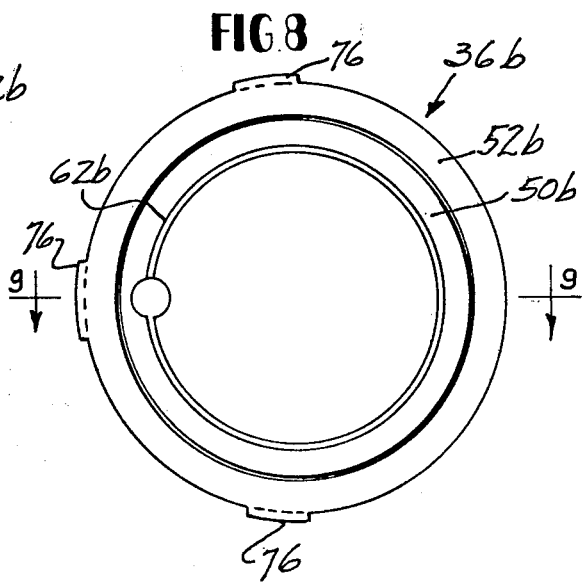

3,961,623

METHOD OF USING A DISPOSABLE ELECTRODE PAD

BACKGROUND OF THE INVENTION

In the use of defibrillating apparatus it is common practice to apply electrodes to the chest of a patient whose heart is fibrillating. To insure adequate electrical contact between the electrode and the body of the patient, the electrode is first coated with an electrically conductive greasy substance, commonly known as electro-gel. This material is somewhat messy to handle, and may not be available at a given moment, and a harassed technician may forget to apply it, thereby resulting in insufficient electrical energy being applied to stop fibrillation of the heart.

SUMMARY OF THE INVENTION

In accordance with the present invention, a generally conventional electrode is provided for attachment to a defibrillating apparatus. A pad impregnated with electro-gel is on the underside of the base sheet, and is covered with a removable, throw-away aluminum foil cover which simultaneously protects the sanitation and integrity of the pad, and allows sufficient electrical contact for a heart to be monitored through the electrode. The cover is torn off and thrown away when it is desired to provide a defibrillating charge to the patient's heart.

BRIEF DESCRIPTION OF THE DRAWINGS

FIG. 1 is a side view of an electrode with the present disposable pad thereon as applied to the skin of a patient;

FIG. 2 is an underside of the disposable electrode pad, with parts being broken away for clarity of illustration;

FIG. 3 is a longitudinal sectional view as taken substantially along the line 3—3 in FIG. 2;

FIG. 4 is a plan view showing the manner in which a plurality of pads is secured to a carrier strip for shipping;

FIG. 5 is a somewhat schematic view showing a modified form of the invention with an electrode and pad being shown in underside view;

FIG. 6 is a view corresponding to FIG. 5 with the parts assembled;

FIG. 7 is a side view of a modified form of the present disposable electrode pad;

FIG. 8 is an underside view thereof;

FIG. 9 is a side view of the pad of FIGS. 7 and 8 assembled with a novel electrode structure;

FIG. 10 shows the electrode structure in retracted position for receipt of the pad; and FIG. 11 shows the electrode structure before retraction and before insertion of the pad.

DETAILED DISCLOSURE

Turning now in greater detail to the figures of the drawings, and first to FIGS. 1–3, there will be seen an electrode carrier or holder 20 having a base 22 and a handle 24. The handle 24 is provided with a thumb button 26 for closing an internal switch to complete the circuit to the electrode. A flexible wire or the like lead 28 leads from the electrode holder to the defibrillating apparatus.

An electrode 30 (FIG. 3) comprises an essentially flat, circular plate 32 of conductive metal, such as aluminum, stainless steel, etc. The plate is provided with an integral stud 34 having a restriction 35 adjacent the upper end thereof. The stud is designed to be received in a socket having a spring detent near the upper end thereof to latch in the restriction 35, and thus to hold the electrode 30 in the electrode holder as shown in FIG. 1.

A disposable electrode pad in accordance with the present invention is adhesively secured to the underside of the electrode plate 32 as shown in FIGS. 1 and 3. The pad, hereinafter identified by numeral 36 comprises a base sheet 38 of conductive material, such as aluminum foil. The base sheet is provided with a wide ring of adhesive material 40 to secure it to the outer face of the electrode plate 32. The central portion of the base sheet or plate 38 is embossed as indicated at 42 to insure good electrical contact with the electrode plate 32 so that it cannot be insulated therefrom by the adhesive material. A disposable pad 44 is formed integral with the base sheet for tearing the pad from the electrode after it has served its purpose.

Beneath or below the base sheet 38 there is provided a pad 46 impregnated with electrically conductive greasy material, commonly known as electro-gel. The pad is secured to the base sheet 44 by an adhesive ring 48, and it will be understood that the adhesion can be effected before the pad is impregnated with the electro-gel, or that an adhesive would be used that is used that is compatible with the electro-gel.

Finally, an aluminum foil cover plate or sheet 50 is provided on the underside of the pad. The periphery of the cover sheet 50 is offset upwardly as a ring 52 which is secured to the underside of the base sheet 38 by an adhesive ring 54. A gel tab 56 extends outwardly from the cover ring 52 for tearing the cover ring from the base sheet. In this connection it is important to note that the adhesive ring 54 between the cover sheet 50 and the base sheet 38 is of smaller area than the adhesive 40 between the base sheet and the electrode plate 32, whereby to insure against accidental pulling of the entire pad assembly from the electrode when the gel tab is pulled to remove the cover.

With reference to FIG. 4, there will be seen a paper or the like carrier strip or sheet 58 having a release agent thereon, such as of plastic material. A plurality of pad assemblies 30 is secured to the carrier strip 58 by the adhesive 40. However, due to the release agent on the surface of the carrier strip the pad assemblies are readily removed therefrom without damage to the adhesive, which adhesive then is used to secure each pad assembly to an electrode.

With the pad assembly secured to an electrode as in FIGS. 1 and 3 the cover sheet 50 may be impressed against the skin 60 of the chest of a patient. The conductive engagement is sufficient to allow the heartbeat of the patient to be monitored in this manner. If it should become necessary to defibrillate the heart of the patient, the technician need only pull on the gel tab 56 to remove the cover sheet 50, whereby the electro-gel impregnated pad is pressed against the skin of the patient's chest, and the thumb button 26 is depressed to cause one or more electrical charges to be impressed on the fibrillating heart, whereby to defibrillate. After the defibrillation has been successfully accomplished, the technician need only pull on the disposing tab 44 to remove the entire pad assembly from the electrode, whereupon it can be thrown in the waste basket, and subsequently supplanted by another pad assembly where it will be fresh and sanitary.

A modification of the invention is shown in FIGS. 5 and 6. The electrode 30 remains as before. The pad assembly 36a remains functionally as before, accordingly being identified by the same number, but with the suffix a. The distinguishing features are that there is no adhesive on the base sheet 38a which is of rectangular configuration. The sheet may be of slightly heavier foil than in the initially disclosed form of the invention, and the corners thereof are folded over at 60 to secure the pad assembly on the plate 32 of the electrode 30. A further distinction is that rather than having an adhesively secured cover sheet with the adhesive coming loose to release the sheet, there is provided a tear string 62 for tearing off and removing a major portion of the cover sheet 50a.

A further modified form of pad assembly 36b is shown in FIGS. 7 and 8. This pad assembly comprises a base sheet 40b of aluminum foil with a cover sheet 50b adhesively secured thereto. The cover sheet is provided with a tear strip or string 62b as in the last previous embodiment of the invention.

This form of the invention is used with a modified electrode, comprising a mounting stud 34b similar to that previously discussed, and a circular or disc-like plate 32b. A retainer 64 comprises a top disc 66 having an aperture 68 therein fitting over the stud 34b. A compression spring 70 encircles the stud between the plate 32b and the disc 66 to urge the retainer 64 up along the stud 34b. A partial peripheral wall 72 depends from the disc 66, and is provided with notches 74 for receiving circumferential protuberances 76 on the pad assembly base for proper positioning. Finally, the retainer comprises a ring 78 joined to the wall 72 and of proper internal diameter to permit the pad assembly 36b to protrude through the ring while the upper surface thereof is held against the undersurface of the plate 32b by the pressure of the spring 70.

In using the form of the invention shown in FIGS. 7–11, the retainer 64 is pushed down against the action of the spring from the position of FIG. 11 to the position of FIG. 10 whereupon the pad assembly 36b is inserted laterally. The retainer is then released, and the ring portion 78 thereof clamps the pad assembly against the underside of the electrode plate 32b, as shown in FIG. 9.

It will now be apparent that we have disclosed a disposable electrode pad for use with defibrillating electrodes which is neat, simple, and sanitary to handle, and which is substantially instantaneously brought into use with electro-gel in contact with the patient's body. The pad is thereafter readily thrown away to permit use of another pad for a subsequent defibrillating operation. The materials used in the manufacture of the pad are inexpensive and readily available in commerce, whereby the pad itself is relatively inexpensive to manufacture and may be considered 100% disposable without being uneconomic.

The specific examples of the invention as herein shown and described are for illustrative purposes. Various changes in structure will no doubt occur to those skilled in the art, and will be understood as forming a part of the present invention, insofar as they fall within the spirit and scope of the appended claims.

The invention is claimed as follows:

1. The method of using a monitoring and defibrillating electrode having a disposable electrode pad thereon impregnated with an electrically conductive gel and covered with a conductive metallic foil which comprises pressing said foil against the skin of a patient's chest, monitoring the heartbeat of such patient through the electrode and the foil, and, in the event of detecting fibrillating of the heart of said patient, at least partially removing said foil and directly contacting the skin of said patient's chest with said electrode pad containing the electrically conductive gel, applying a defibrillating electrical charge to the heart of said patient through the electrode and the electrically conductive gel, and thereafter discarding said disposable electrode pad and substituting a new one on said electrode.

* * * * *